US010641692B2

(12) United States Patent
Hwang

(10) Patent No.: US 10,641,692 B2
(45) Date of Patent: May 5, 2020

(54) MEASUREMENT APPARATUS FOR MEASURING A RELATIONSHIP BETWEEN A DEGREE OF CURE AND A SPECIFIC VOLUME OF A PACKAGING MATERIAL

(71) Applicant: U-CAN DYNATEX INC., Taichung (TW)

(72) Inventor: Sheng-Jye Hwang, Tainan (TW)

(73) Assignee: U-CAN DYNATEX INC., Taichung (TW)

( * ) Notice: Subject to any disclaimer, the term of this patent is extended or adjusted under 35 U.S.C. 154(b) by 315 days.

(21) Appl. No.: 15/869,270

(22) Filed: Jan. 12, 2018

(65) Prior Publication Data

US 2018/0284001 A1     Oct. 4, 2018

Related U.S. Application Data

(60) Provisional application No. 62/479,441, filed on Mar. 31, 2017.

(30) Foreign Application Priority Data

Jun. 2, 2017    (TW) .............................. 106118259 A

(51) Int. Cl.
*G01M 5/00*     (2006.01)
*G01N 9/00*     (2006.01)
(Continued)

(52) U.S. Cl.
CPC ........... *G01N 9/00* (2013.01); *B29C 35/0288* (2013.01); *B29C 35/0294* (2013.01); *B29C 37/005* (2013.01); *G01B 5/30* (2013.01); *G01N 3/08* (2013.01); *G01N 9/02* (2013.01); *G01N 33/442* (2013.01); *G01N 2009/024* (2013.01); *G01N 2203/0003* (2013.01); *G01N 2203/0019* (2013.01); *G01N 2203/0037* (2013.01); *G01N 2203/0085* (2013.01); *G01N 2203/0092* (2013.01); *G01N 2203/023* (2013.01); *G01N 2203/0222* (2013.01);
(Continued)

(58) Field of Classification Search
CPC .............................. G01M 99/007; G01M 5/00
See application file for complete search history.

(56) References Cited

U.S. PATENT DOCUMENTS 5,520,057 A *   5/1996  Nakamura ............ G01L 5/0085
                                                  73/785
7,614,282 B2 * 11/2009  Eliasson ............... G01M 3/363
                                                  73/49.3

* cited by examiner

*Primary Examiner* — Lisa M Caputo
*Assistant Examiner* — Alex T Devito
(74) *Attorney, Agent, or Firm* — Amin, Turocy & Watson, LLP

(57) ABSTRACT

An apparatus for measuring a degree of cure and a specific volume of a packaging material is provided, including: an upper load module configured for driving the rotation of an upper ball screw via an upper servo motor such that a force plate coupled to the upper ball screw moves downward and is thus positioned; a lower load module having a lower ball screw operating and moving via a lower servo motor such that a load joint group connected to the lower ball screw generates a corresponding displacement; an upper film cavity module connected to the upper load module; and a lower film cavity module disposed on the lower load module. The displacement of the load joint group enables a push rod to move upward. A heating pipe keeps constant the temperature of a subject to be measured in a cavity of the lower film cavity module.

12 Claims, 17 Drawing Sheets

(51) Int. Cl.
*B29C 35/02* (2006.01)
*G01B 5/30* (2006.01)
*B29C 37/00* (2006.01)
*G01N 3/08* (2006.01)
G01N 9/02 (2006.01)
G01N 33/44 (2006.01)

(52) U.S. Cl.
CPC ............... *G01N 2203/0252* (2013.01); *G01N 2203/0284* (2013.01); *G01N 2203/0682* (2013.01)

MEASUREMENT APPARATUS FOR MEASURING A RELATIONSHIP BETWEEN A DEGREE OF CURE AND A SPECIFIC VOLUME OF A PACKAGING MATERIAL

BACKGROUND

1. Technical Field

The present disclosure relates to techniques for testing packaging materials, and, more particularly, to a measurement apparatus for measuring a relationship between a degree of cure and a specific volume of a packaging material.

2. Description of Related Art

In recent years, the semiconductor industry has undergone rapid development, and integrated circuits (ICs) are packaged to have low profile and compact size. Semiconductor dies of ICs are packaged and protected from contamination and damage.

ICs can have a ceramic package or a plastic package. A ceramic package is highly stable and reliable, but expensive, and is thus not very popular in the market. By contrast, a plastic package generally uses an epoxy molding compound (EMC), and is cheap and more popular than the plastic package. However, the plastic package is poor in air tightness, and suffers from low stability and reliability. Epoxy molding compound is a thermosetting material, and causes a cross-linking reaction when heated above a certain temperature. During the cross-linking reaction, plastic molecules are solidified and bonded to one another to release heat, and the compound is cured. The cured compound turns into a new material and have a different nature.

Bridging (solidification) phenomenon occurs between the molecules of epoxy resin, and heat is released. During the curing of the epoxy resin, temperature and pressure are closely related to the degree of cure, and thus affect the specific volume of the epoxy resin. However, most researches focus their warping analysis of the finished products on temperature difference, without further taking the curing reaction of the epoxy resin into considerations.

Therefore, there is a need for a measurement mechanism of the degree of cure of a packaging material, especially for determining the relationship between the degree of cure and the specific volume of the packaging material at different temperatures and pressures.

SUMMARY

The present disclosure provides a mechanism for measuring a relationship between a degree of cure and a specific volume of a packaging material. By devising a Pressure-Volume-Temperature-Curing (P-V-T-C) measurement apparatus, a packaging material such as epoxy resin is held under constant temperature and pressure to find the effect of degree of cure on the specific volume, and a P-T-V-C relationship is then established for calculation of warpage in future packaging processes.

The present disclosure provides a measurement apparatus for measuring a relationship between a degree of cure and a specific volume of a packaging material, which may include: an upper load module provided at a top of the apparatus and including an upper servo motor, an upper ball screw and a force plate, the upper servo motor driving the upper ball screw into rotation via a belt, such that the force plate coupled to the upper ball screw moves downward and is positioned in place; a lower load module provided at a bottom of the apparatus and including a lower servo motor, a lower ball screw and a load joint group having a push rod, the lower ball screw being driven by operations of the lower servo motor, such that the load joint group coupled to the lower ball screw creates a corresponding displacement; an upper film cavity module coupled to the force plate of the upper load module; and a lower film cavity module provided on the lower load module for partially and slidably receiving the push rod of the load joint group, such that the push rod moves up with the displacement of the load joint group, wherein the lower film cavity module includes a cavity and a heating pipe for heating and maintaining a subject to be measured in the cavity at a constant temperature, wherein the upper film cavity module moves down through the force plate and the push rod in the lower film cavity module moves up, such that a constant pressure is applied to the subject to be measured in the cavity, and a change in volume per unit time of the subject to be measured is measured by an optical measuring unit provided on the lower load module near the cavity.

The above measurement apparatus may further include a controller for controlling operations of the upper servo motor, the lower servo motor, and the heating pipe based on the temperature, a load, and a displacement of the subject to be measured.

In an embodiment, the controller adjusts the temperature of the heating pipe using a temperature controller.

In another embodiment, the temperature controller obtains the temperature of the subject to be measured using a temperature sensor provided in the cavity.

In yet another embodiment, the controller obtains forces exerted on the subject to be measured using a load sensor provided in each of the upper film cavity module and the lower film cavity module.

In still another embodiment, the controller converts the forces exerted on the subject to be measured into a voltage output, and the load of the subject to be measured is calculated based on the magnitude of the voltage.

In an embodiment, the measurement apparatus further includes a data processing module connected to the controller for calculating a volume shrinkage ratio of the subject to be measured based on the change in volume of the subject to be measured to obtain a relationship between the volume shrinkage ratio and the degree of cure of the subject to be measured.

In still another embodiment, the optical measuring unit is an optical ruler for measuring a change in height of the subject to be measured.

In still another embodiment, the upper load module further includes a motor pulley coupled to the upper servo motor and a driven pulley coupled to the upper ball screw, with the belt surrounding the motor pulley and the driven pulley.

In an embodiment, the measurement apparatus may further include an exterior frame for enclosing the upper load module, the lower load module, the upper film cavity module and the lower film cavity module.

In still another embodiment, the load joint group is provided at the top end of the lower ball screw, and the load joint group produces an upward displacement according to an upward movement of the lower ball screw. Alternatively, the load joint group is provided at a side of the lower ball screw, and the load joint group produces an upward displacement along with an upward movement of the lower ball screw.

Compared to the prior art, the measurement apparatus for measuring a relationship between a degree of cure and a specific volume of a packaging material according to the present disclosure holds the subject to be measured in a constant pressure environment through the displacements of the upper film cavity module and the lower film cavity module, and holds the subject to be measured in a constant temperature through the heating pipe. By monitoring the temperature and the pressure, the change in volume of the subject to be measured per unit time can be measured, and in turn the change in volume of the packaging material. This can be used subsequently for deducing the P-V-T-C relationship.

BRIEF DESCRIPTION OF THE DRAWINGS

FIGS. 2A to 2C depict the framework of an upper load module of the measurement apparatus for measuring the relationships between the degree of cure and the specific volume of packaging materials, wherein FIG. 2A is an isometric view of the upper load module, FIG. 2B is a right side view of the upper load module, and FIG. 2C is a front view of the upper load module;

FIGS. 3A to 3D depict the framework of a lower load module of the measurement apparatus for measuring a relationship between a degree of cure and a specific volume of a packaging material, wherein FIG. 3A is an isometric view of the lower load module, FIG. 3B is a front view of the lower load module, and FIG. 3C is a cross-sectional view of the lower load module of FIG. 3B along the line A-A shown in FIG. 3B;

FIGS. 4A to 4D depict the framework of an upper film cavity module of the relationship between a degree of cure and a specific volume of a packaging material according to the present disclosure, wherein FIG. 4A is an isometric view of the upper film cavity module, FIG. 4B is a front view of the upper film cavity module, and FIGS. 4C and 4D are cross-sectional views of the upper film cavity module of FIG. 4B along the lines B-B and A-A, respectively;

FIGS. 5A to 5C depict the framework of a lower film cavity module of the measurement apparatus for measuring a relationship between a degree of cure and a specific volume of a packaging material according to the present disclosure, wherein FIG. 5A is an isometric view of the lower film cavity module, FIG. 5B is a side view of the lower film cavity module, and FIG. 5C is a cross-sectional view of the lower film cavity module of FIG. 5B along the line A-A shown in FIG. 5B;

DETAILED DESCRIPTION OF THE EMBODIMENTS

The present disclosure is described by the following specific embodiments. Those with ordinary skills in the arts can readily understand other advantages and functions of the present disclosure after reading the disclosure of this specification. The present disclosure may also be practiced or applied with other different implementations. Based on different contexts and applications, the various details in this specification can be modified and changed without departing from the spirit of the present disclosure.

Figure 1A:
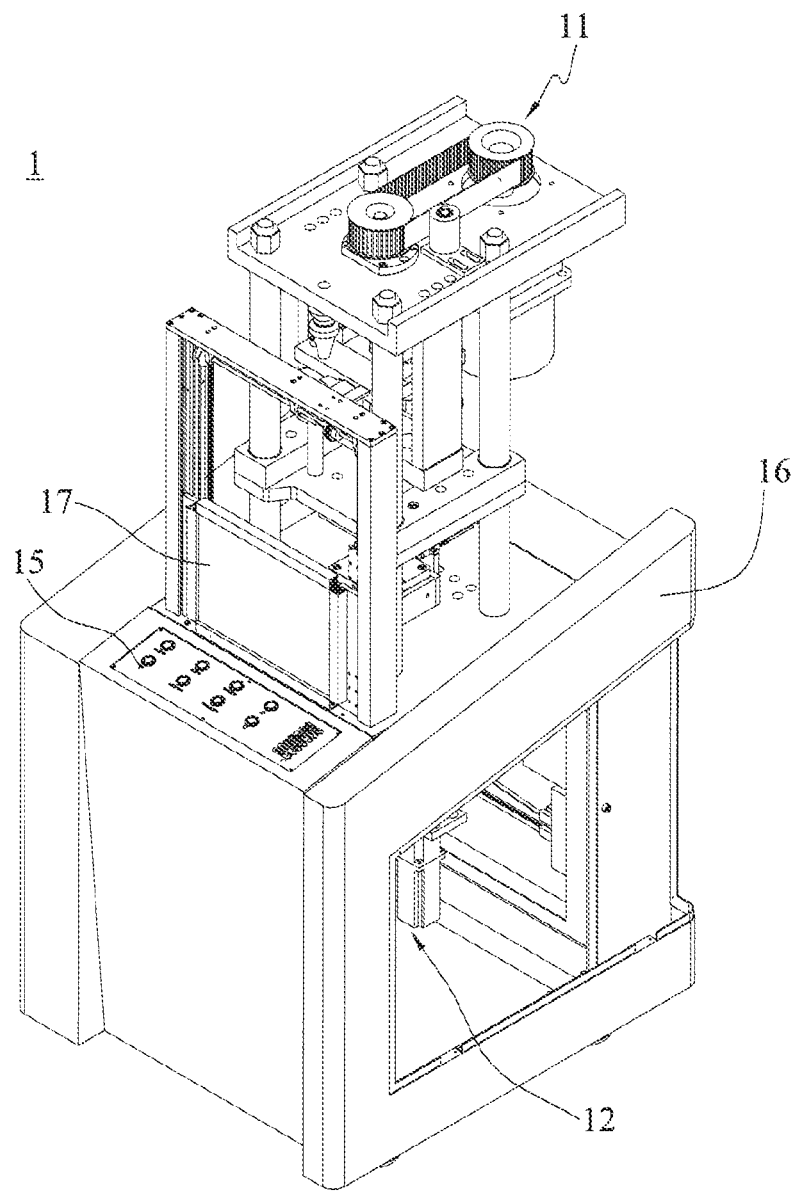
FIGS. 1A and 1B are an isometric view and a side view depicting the framework of a measurement apparatus for measuring a relationship between a degree of cure and a specific volume of a packaging material, respectively.
Figure 1B:
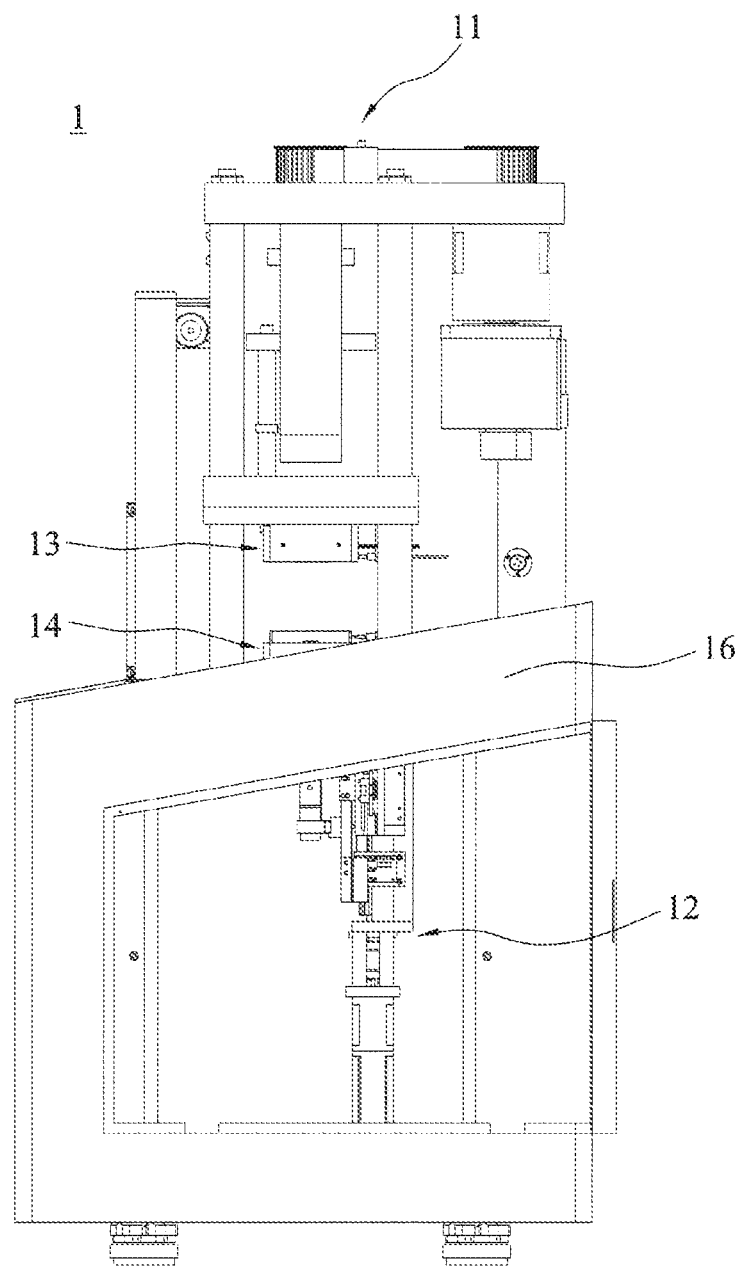

Referring to FIGS. 1A and 1B, an isometric view and a side view of a measurement apparatus for measuring a relationship between a degree of cure and a specific volume of packaging materials are shown, respectively. Simply put, the present disclosure is aimed to obtain the relationships between the volume shrinkage and the degree of cure of a packaging material to be used as a reference for warpage during packaging in the future. The present disclosure thus wishes to obtain the changes in the volume of the packaging material by taking both the temperature and the pressure into consideration. Then, the relationships between the volume shrinkage and the degree of cure can be deduced by numerical generalization. Therefore, the present disclosure proposes a measurement apparatus for measuring the change in volume of a packaging material under controlled temperatures and pressures.

As shown in FIGS. 1A and 1B, FIG. 1A is an isometric view of the measurement apparatus, and FIG. 1B is a side view of the measurement apparatus. The measurement apparatus for measuring a relationship between a degree of cure and a specific volume of a packaging material of the present disclosure may include an upper load module 11, a lower load module 12, an upper film cavity module 13, and a lower film cavity module 14.

In addition to a measurement apparatus for measuring a relationship between a degree of cure and a specific volume of a packaging material 1, a control panel 15 is provided at the bottom front of the measurement apparatus to allow user to input data. The lower load module 12 is provided in a lower exterior frame 16. The lower film cavity module 14 is provided above the lower load module 12. The upper film cavity module 13 is provided below the upper load module 11. An upper exterior frame (not shown) is provided above the lower exterior frame 16 for enclosing the upper load module 11, the upper film cavity module 13 and the lower film cavity module 14. When the upper exterior frame (not shown) is laid on top of the lower exterior frame 16, a subject to be measured can be placed into the measurement apparatus for measuring a relationship between a degree of cure and a specific volume of a packaging material 1 through an operating window 17.

The upper load module 11 can drive the upper film cavity module 13 to have a downward displacement. The subject to be measured is placed in the lower film cavity module 14. When the upper load module 11 and the lower film cavity module 14 move towards each other, the subject to be measured is under certain pressure in the lower film cavity module 14. In addition, ambient temperature of the subject to be measured can also be adjusted, so that it is in an environment of a constant temperature. As such, the changes in volume of the subject to be measured can be measured at different temperatures and pressures.

The details of the upper load module 11, the lower load module 12, the upper film cavity module 13 and the lower film cavity module 14 are illustrated below.

Figure 2A:
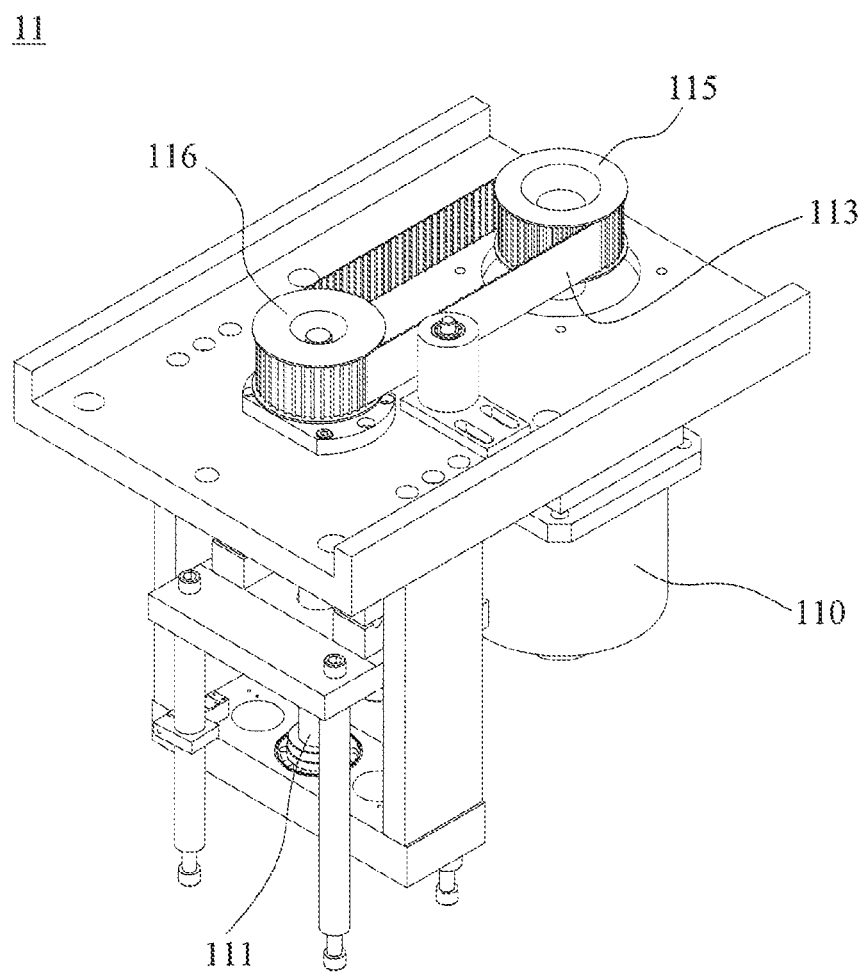
Figure 2B:
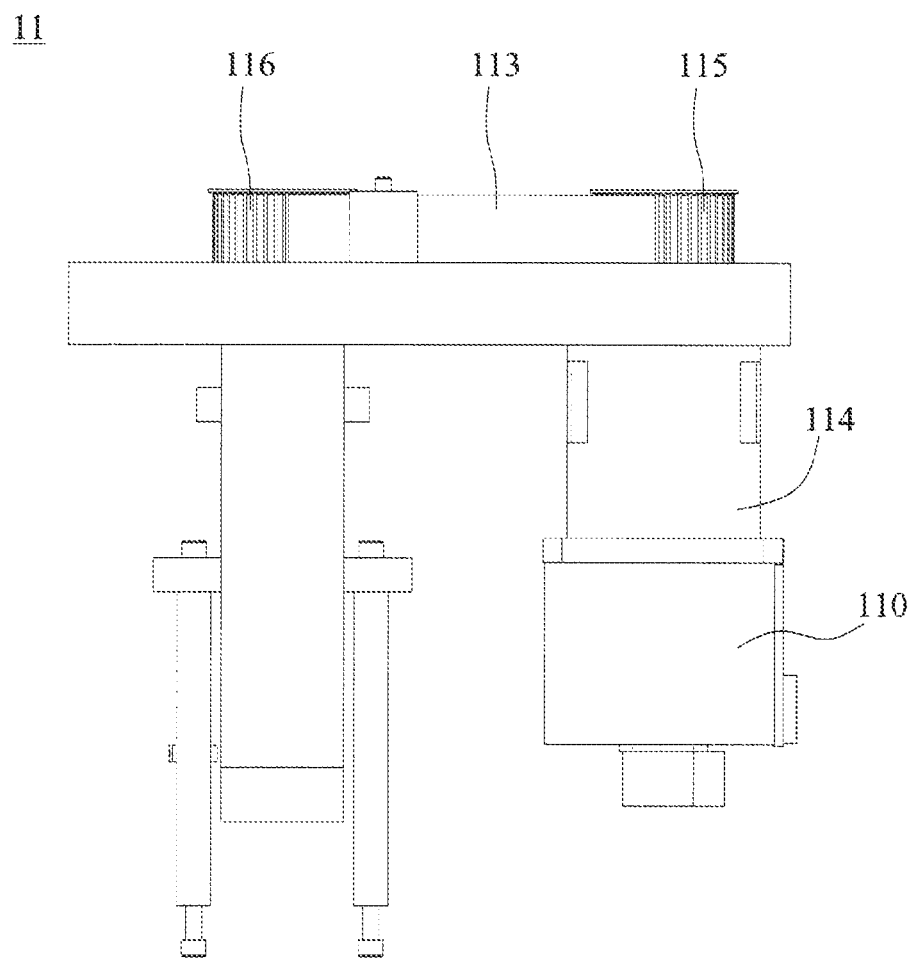
Figure 2C:
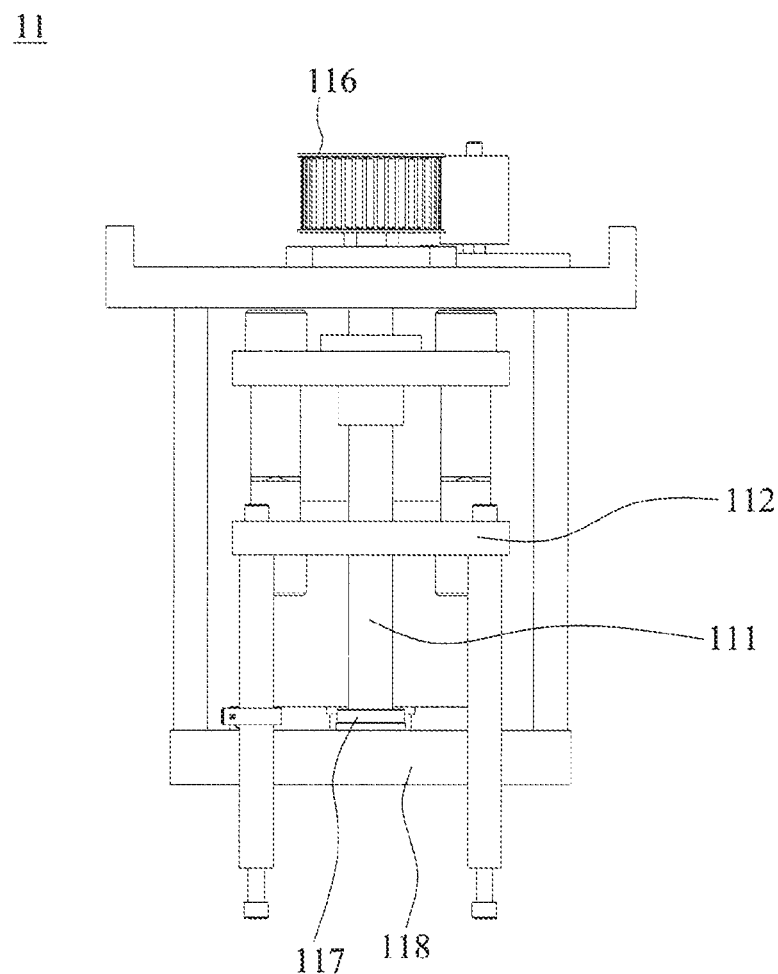

Referring to FIGS. 2A to 2C, the framework of the upper load module of the measurement apparatus for measuring the relationships between the degree of cure and the specific volume of packaging materials is shown, wherein FIG. 2A is an isometric view of the upper load module, FIG. 2B is a right side view of the upper load module, and FIG. 2C is a front view of the upper load module.

As shown in FIGS. 2A to 2C, the upper load module 11 is located generally at the upper end of the measurement apparatus for measuring a relationship between a degree of cure and a specific volume of a packaging material 1, which includes an upper servo motor 110, an upper ball screw 111 and a force plate 112. The upper servo motor 110 drives the rotation of the upper ball screw 111 through a belt 113, such that the force plate 112 coupled to the upper ball screw 111 moves downward and is thus positioned.

Referring to FIG. 2B, a motor pulley 115 is movably coupled to the upper servo motor 110. The upper servo motor 110 rotates and drives the motor pulley 115 into rotation, and in turns a driven pulley 116 is driven through the belt 113. The driven pulley 116 and the upper ball screw 111 are movably coupled, such that when the upper servo motor 110 rotates, the upper ball screw 111 moves downwards. The upper ball screw 111 is coupled to a bearing securing plate 118 via a joint bearing 117, such that the force plate 112 moves downwards. The force plate 112 is coupled to the upper film cavity module 13 in FIG. 1B, so that the upper film cavity module 13 moves to a required position, thereby positioning the upper film cavity module 13.

In addition, a speed reducer 114 can be provided between the upper servo motor 110 and the motor pulley 115 to adjust the rotational speed output by the upper servo motor 110.

Figure 3A:
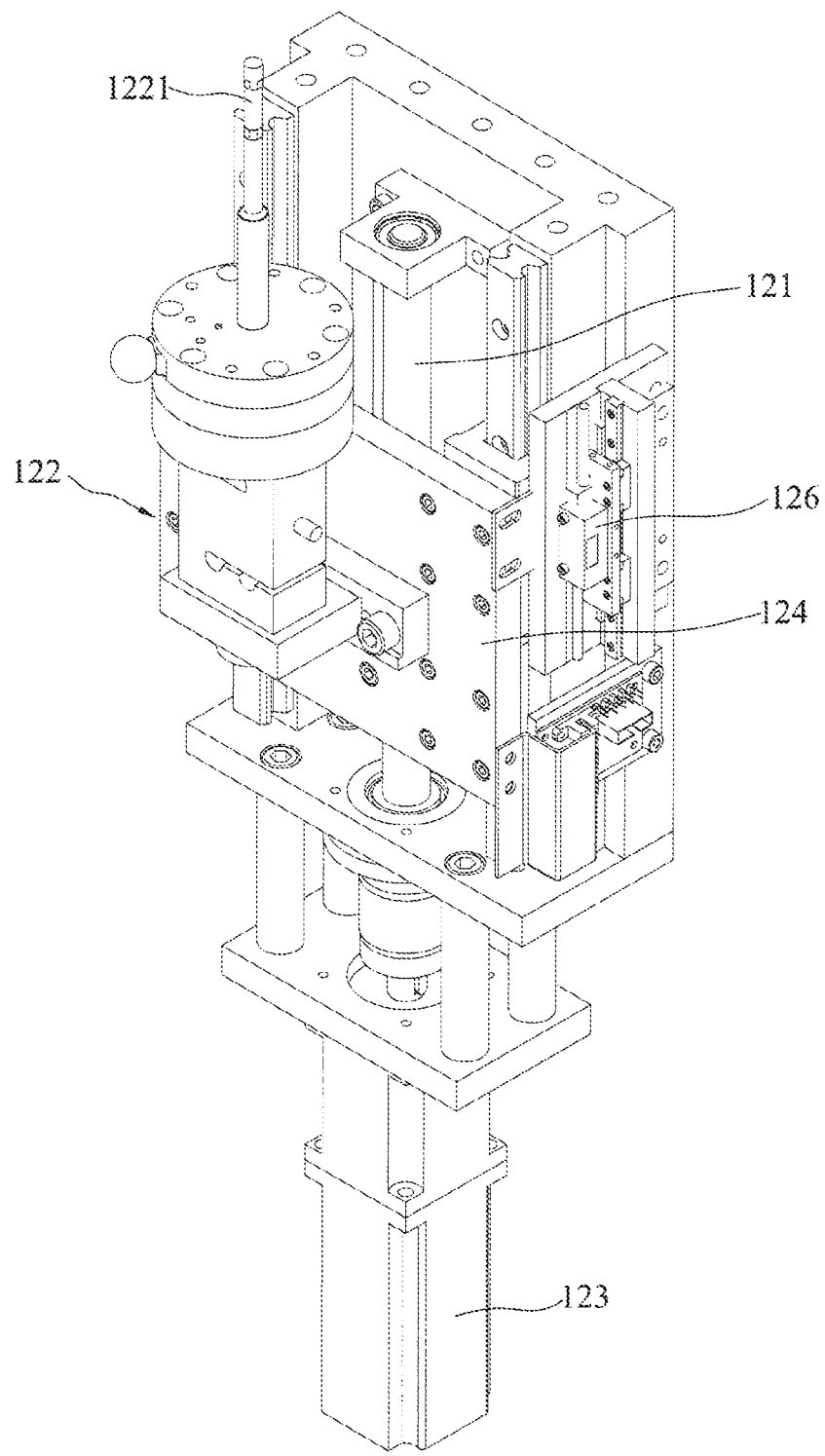
Figure 3B:
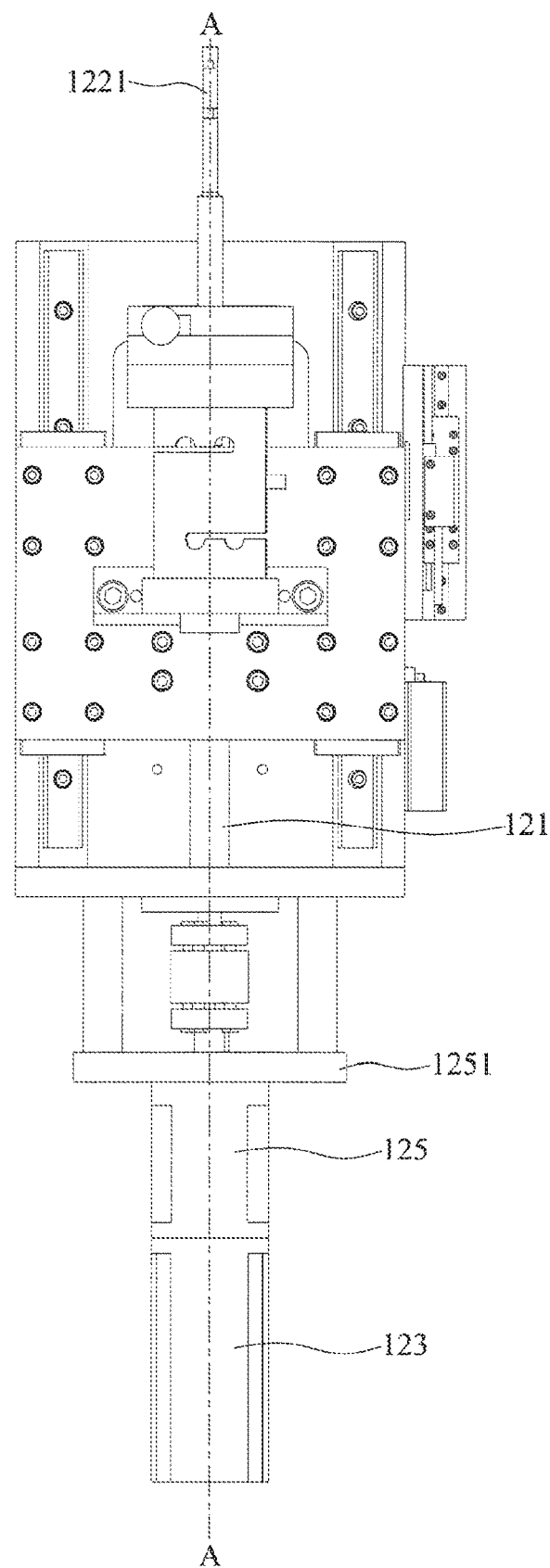
Figure 3C:
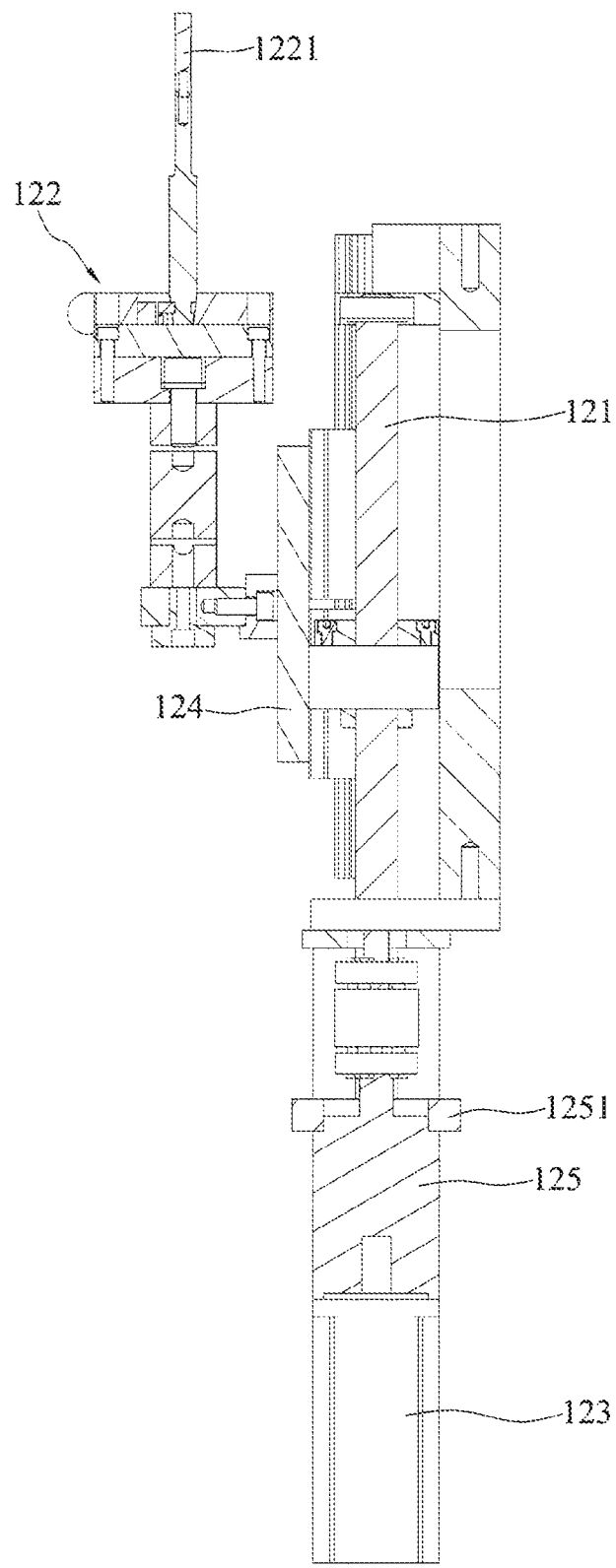

Referring to FIGS. 3A to 3D, the framework of the lower load module of the measurement apparatus for measuring a relationship between a degree of cure and a specific volume of a packaging material is shown, wherein FIG. 3A is an isometric view of the lower load module, FIG. 3B is a front view of the lower load module, and FIG. 3C is a cross-sectional view of the lower load module of FIG. 3A along a line A-A.

As shown in FIGS. 3A to 3D, the lower load module 12 includes a lower ball screw 121 and a load joint group 122, wherein the lower ball screw 121 produces an upper or lower displacement according to the operations of a lower servo motor 123, such that the load joint group 122 coupled to the lower ball screw 121 produces a corresponding movement. That is, when the lower ball screw 121 moves upwards, the load joint group 122 also moves upwards.

More specifically, the load joint group 122 is provided at the side of the lower ball screw 121, and provided on the lower load module 12 via a lower load base 124, wherein the load joint group 122 moves upwards along with the upward displacement of the lower ball screw 121.

In addition, a push rod 1221 of the load joint group 122 is inserted into the lower film cavity module 14 of FIG. 1B, such that when the push rod 1221 moves, a space is created in the lower film cavity module 14 for receiving a subject to be measured, or a push force is applied to the subject to be measured.

The lower load module 12 further includes a speed reducer 125 provided on the lower servo motor 123 via a speed reducer securing plate 1251 for adjusting the rotational speed output by the lower servo motor 123.

The lower load module 12 further includes an optical measuring unit 126 provided at a side of the lower load module 12 near a cavity in the lower film cavity module 14. The optical measuring unit 126 can be an optical ruler for measuring the size of displacement of the load joint group 122, and in turn obtaining the change in height of the subject to be measured. Simply put, the change in height of the subject to be measured can be deduced from the displacement of the load joint group 122.

Figure 3D:
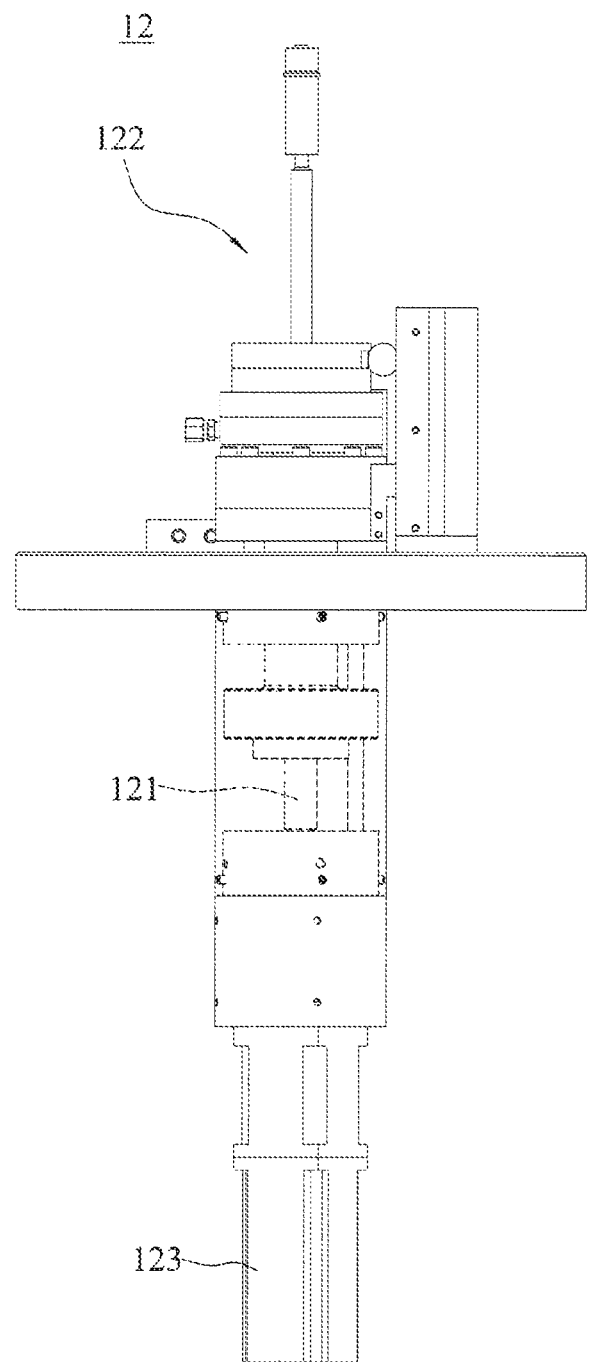

Moreover, as shown in FIG. 3D, another embodiment of the lower load module 12 is shown. In FIGS. 3A to 3C, the load joint group 122 is provided at the side of the lower ball screw 121, but in this embodiment, the load joint group 122 is provided on top of the lower ball screw 121. In other words, the lower ball screw 121 moves up or down according to the operations of the lower servo motor 123, and in turn a corresponding movement is produced in the load joint group 122 on top of the lower ball screw 121. Either one of the above two designs of the lower load module 12 can be adopted according to the needs, as long as the load joint group 122 is moved to a required position.

Figure 4A:
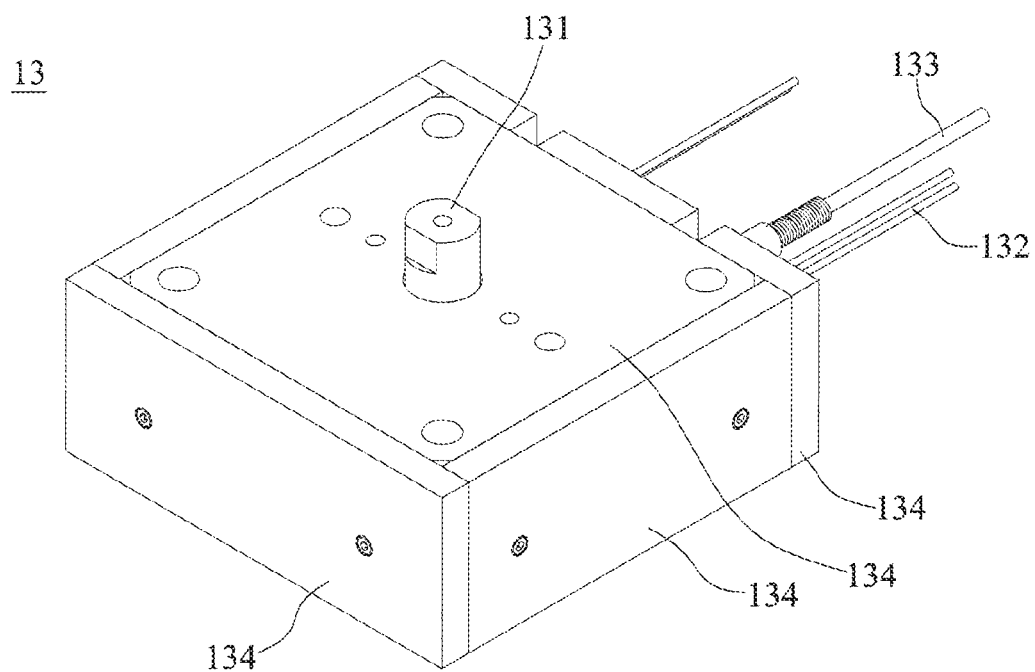
Figure 4B:
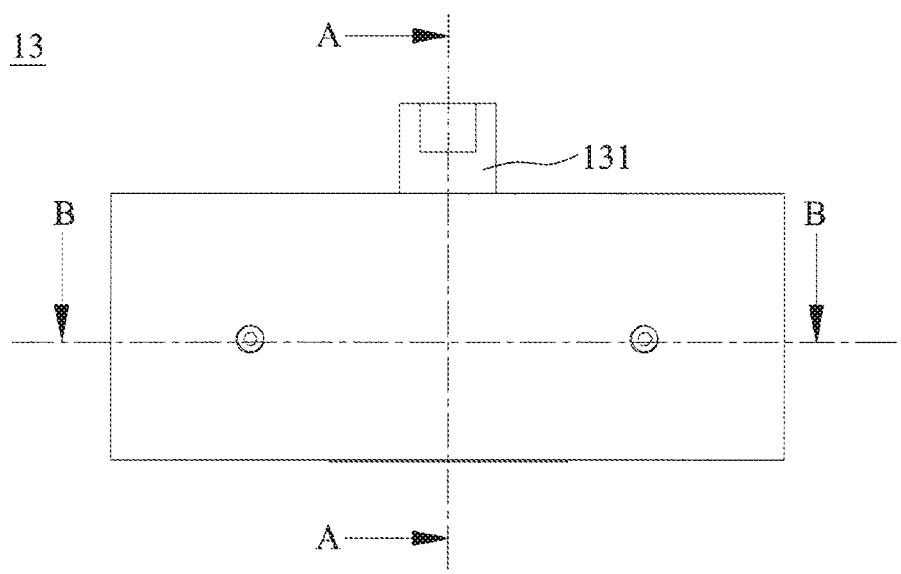
Figure 4C:
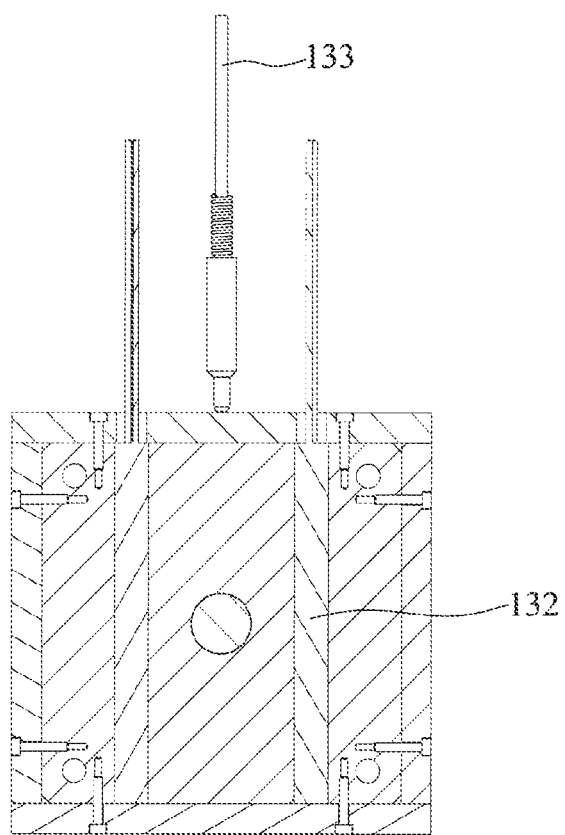
Figure 4D:
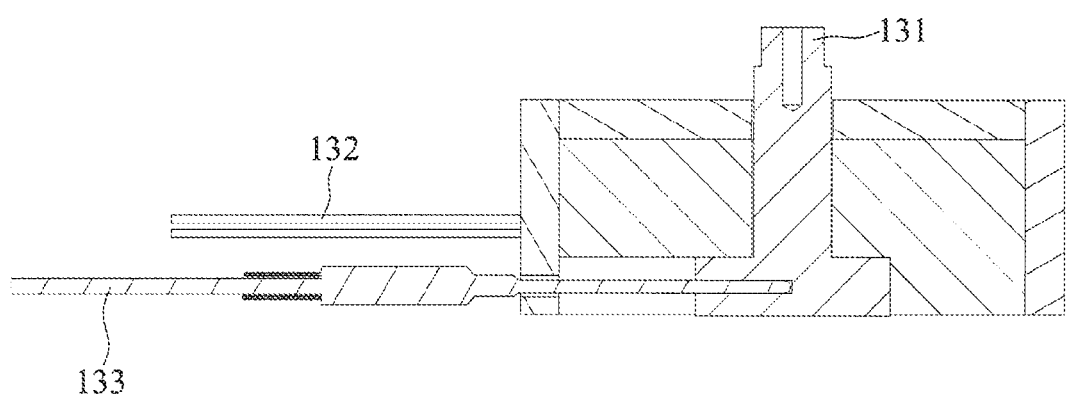

Referring to FIGS. 4A to 4D, the framework of the upper film cavity module of the a relationship between a degree of cure and a specific volume of a packaging material according to the present disclosure is shown, wherein FIG. 4A is an isometric view of the upper film cavity module, FIG. 4B is a front view of the upper film cavity module, and FIGS. 4C and 4D are cross-sectional views of the upper film cavity module of FIG. 4B along lines B-B and A-A.

As shown in FIGS. 4A to 4D, the upper film cavity module 13 includes an upper film portion 131, a heating pipe 132, a temperature sensor 133 and a heat shield 134. The upper film portion 131 is coupled to the upper load module 11 of FIG. 1B, so that the upper film cavity module 13 moves along with the movement of the upper load module 11. The upper film cavity module 13 is provided with the heating pipe 132 therein. The heating pipe 132 allows the upper film cavity module 13 overall to be maintained at a certain temperature. Thus, the subject to be measured is prevented from having temperature variation due to proximity to different temperature areas of the upper film cavity module 13 when the upper film cavity module 13 is pressed against the lower film cavity module 14 containing the subject to be measured (FIG. 1B). The position and type of the heating pipe 132 can be designed according to needs, and can, for example, surround the entire upper film cavity module 13.

The heat shield 134 surrounds the upper film cavity module 13 to prevent heat loss from the upper film cavity module 13. In addition, the temperature of the upper film cavity module 13 can be monitored by the temperature sensor 133. The temperature sensor 133 can be, for example, a temperature measuring stick for sensing the temperature of the upper film cavity module 13 to be used as a basis for adjusting the heating of the heating pipe 132.

Figure 5A:
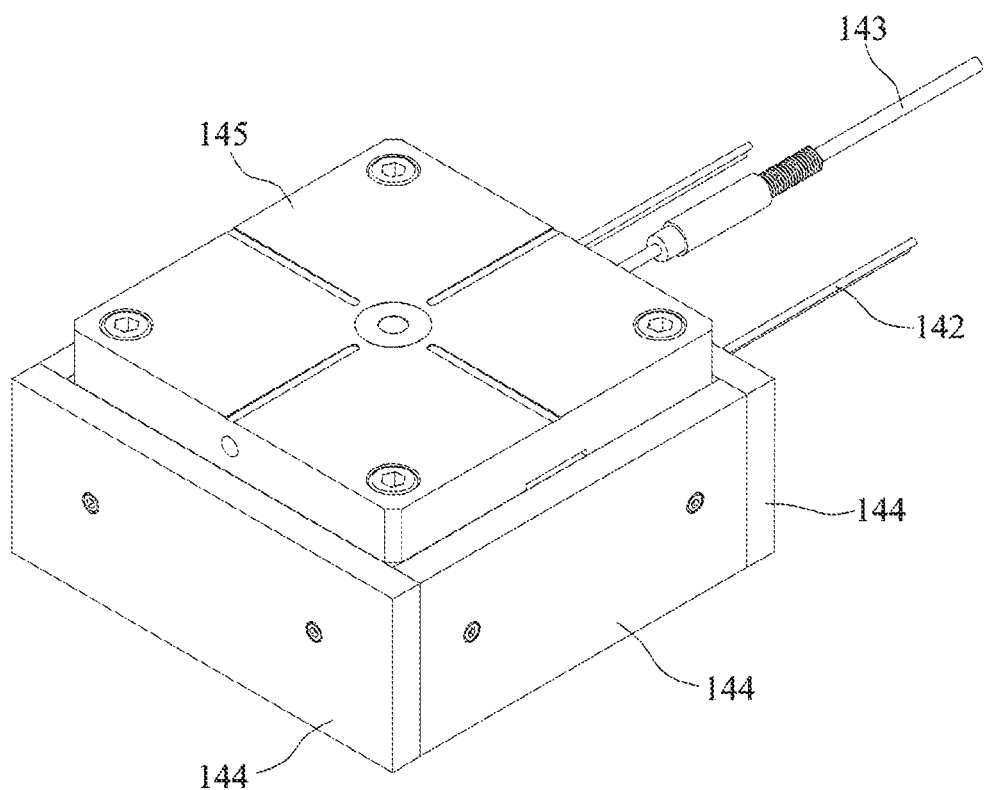
Figure 5B:
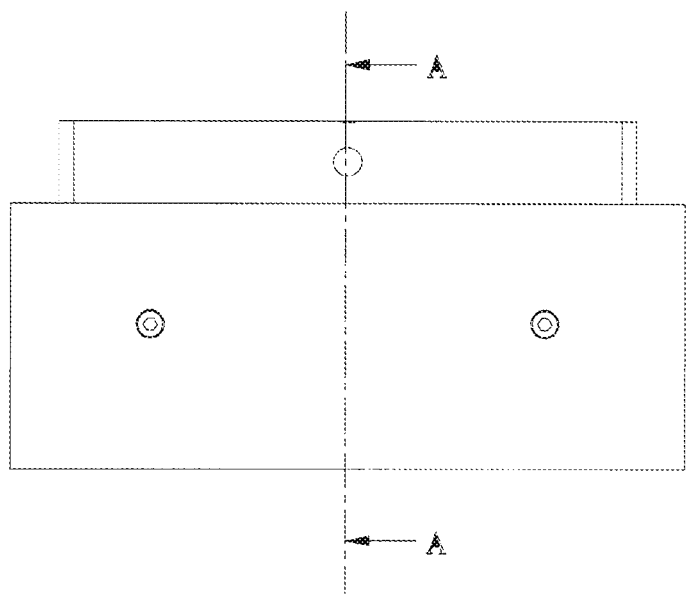
Figure 5C:
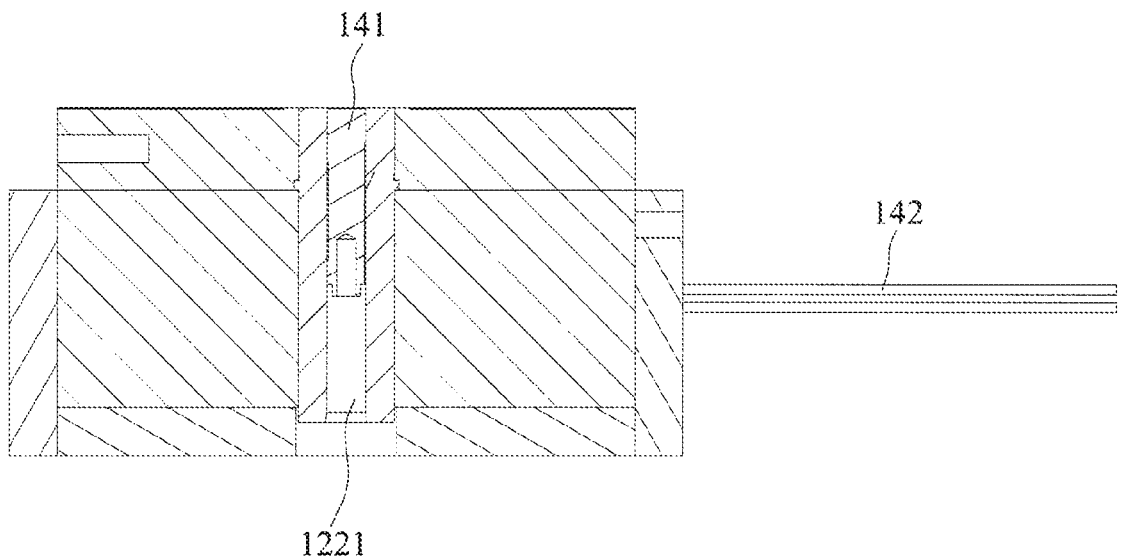

Referring to FIGS. 5A to 5C, the framework of the lower film cavity module of the measurement apparatus for measuring a relationship between a degree of cure and a specific volume of a packaging material of the present disclosure is shown, wherein FIG. 5A is an isometric view of the lower film cavity module, FIG. 5B is a side view of the lower film cavity module, and FIG. 5C are cross-sectional views of the lower film cavity module of FIG. 5B along a line A-A.

The lower film cavity module 14 is provided on the lower load module 12 and the push rod 1221 of the load joint group 122 of the lower load module 12 is partially inserted therein, as shown in FIG. 5C. In addition, the lower load module 12 drives the push rod 1221 of the load joint group 122 to move up or down, wherein the lower film cavity module 14 includes a cavity 141 and a heating pipe 142. The heating of the heating pipe 142 allows the subject to be measured placed inside the cavity 141 to be maintained at a certain temperature. If a constant temperature is required, the temperature monitoring can be used to achieve the constant temperature.

The position and type of the heating pipe 142 can be designed according to needs, and the heating pipe 142 can, for example, surround the entire lower film cavity module 14. Preferably, since the purpose of heating is to keep the subject to be measured at a certain temperature, the heating pipe 142 can be provided near the subject to be measured, e.g., surrounding the subject to be measured. Moreover, the lower film cavity module 14 further includes a temperature sensor 143 for sensing the ambient temperature surrounding the subject to be measured. The heating of the heating pipe 142 can then be adjusted according to the result of sensed temperature.

The lower film cavity module 14 is similarly surrounded by a heat shield 144 to prevent heat loss through thermal conduction. Moreover, the lower film cavity module 14 further includes a lower film portion 145 to support the upper film cavity module thereon. A hole is provided in the center of the lower film portion 145 for receiving the subject to be measured. The hole in the lower film cavity module 14 is the abovementioned cavity 141.

With the combination of the above components, the upper film cavity module 13 moves downwards through the force plate 112, and the push rod 1221 in the lower film cavity module 14 moves upwards, such that the subject to be measured in the cavity 141 is under a certain pressure. In other words, the upper film cavity module 13 acts like a limiter with a downward pressure, while the push rod 1221 in the lower film cavity module 14 provides a upward pressure, so that the subject to be measured in the lower film cavity module 14 is in a predefined pressured environment. With the measurement apparatus of the present disclosure, different pressures and temperatures can be provided, so a change in volume can be measured under different pressures and temperatures. The change in volume per unit time of the subject to be measured can be deduced from a measurement provided by the optical measuring unit 126 (FIG. 3A) of the lower load module 12.

Figure 6:
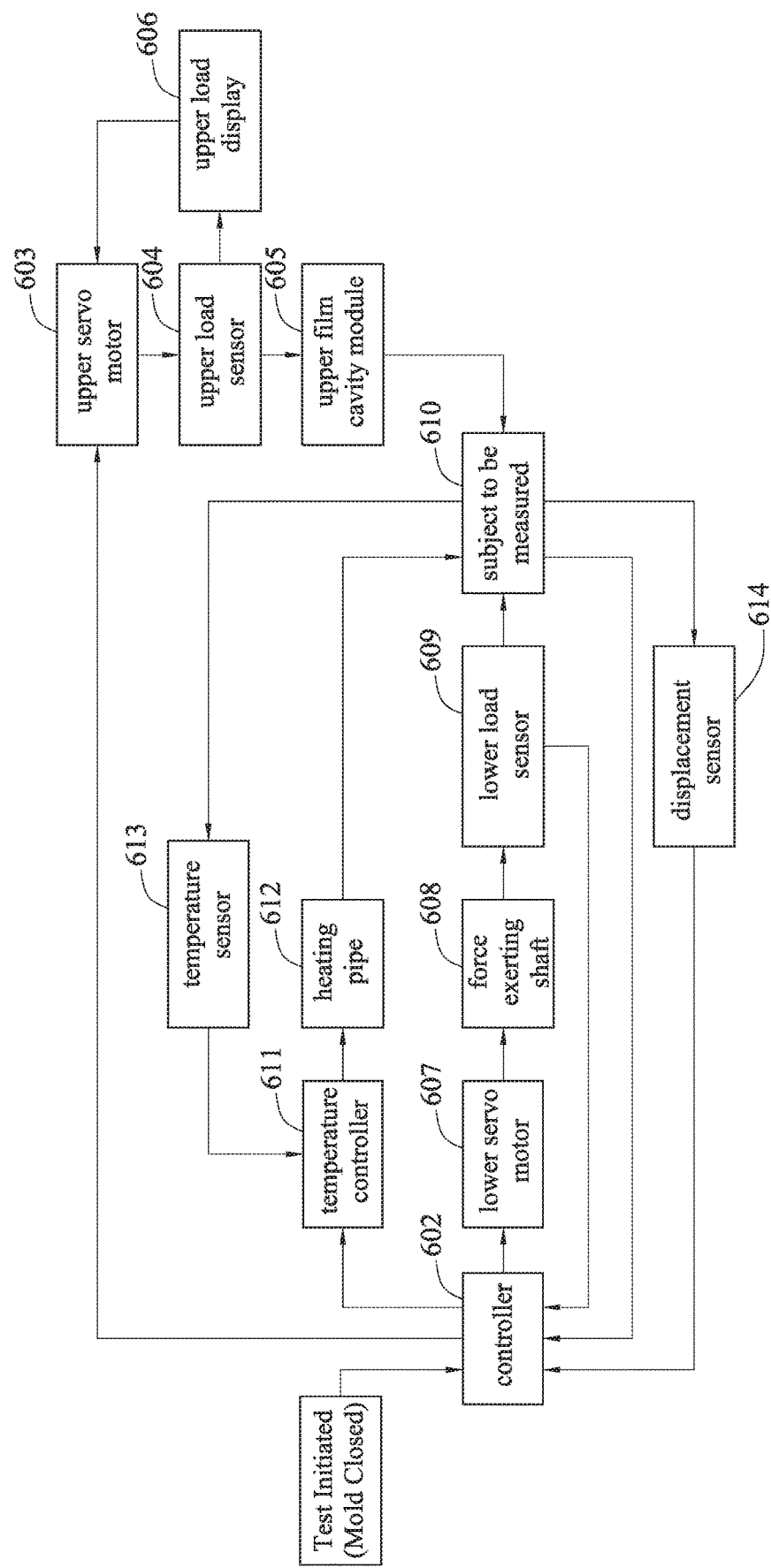
FIG. 6 is a flowchart illustrating operations of the measurement apparatus for measuring a relationship between a degree of cure and a specific volume of a packaging material according to the present disclosure.

Referring to FIG. 6, a flowchart illustrating operations of the measurement apparatus for measuring a relationship between a degree of cure and a specific volume of a packaging material according to the present disclosure is shown. Specifically, a controller can be provided in the measurement apparatus for measuring a relationship between a degree of cure and a specific volume of a packaging material for controlling operations of the upper servo motor, the lower servo motor and the heating pipes based on the temperature, a load and a displacement of the subject to be measured.

As shown, when a test is initiated, a controller 602 performs control of the associated components. At this time, an upper servo motor 603 is instructed to start operation in order to provide energy for downward movement to the upper film cavity module 605. Meanwhile, an upper load sensor 604 is instructed to sense the weight applied. The weight can be displayed via an upper load display 606 if necessary. The operation of the upper servo motor 603 is adjusted if necessary to change the magnitude of the applied force.

When the controller 602 is controlling the upper servo motor 603, it may also be controlling a lower servo motor 607 simultaneously. The controller 602 is able to control the force exerted on a subject to be measured 610 by a force exerting shaft 608 (i.e. the lower ball screw described above), such that the subject to be measured 610 is under pressure. Meanwhile, a lower load sensor 609 can be used for sensing the weight applied, i.e. the force experienced by the subject to be measured 610.

Specifically, the controller 602 is able to convert the force experienced by the subject to be measured 610 into a voltage output, which can then be converted into the load on the subject to be measured 610. Therefore, with the operations of the upper servo motor 603 and the lower servo motor 607, the subject to be measured within the lower film cavity module is under a specific pressure through the joint limiting downward force applied by the upper film cavity module 605 and the upward force applied by the push rod in the lower film cavity module.

The controller 602 can control heating of a heating pipe 612 near the subject to be measured 610 through a temperature controller 611, such that the subject to be measured reaches and maintains at a certain temperature. The ambient temperature of the subject to be measured can be measured by a temperature sensor 613 and reported back to the temperature controller 611. The temperature controller 611 can then adjust the heating of the heating pipe 612 accordingly.

The displacement, i.e., the change in height of the subject to be measured 610 can be measured by a displacement sensor 614. Specifically, the subject to be measured 610 is placed in a confined cylindrical space (i.e., the cavity described above) of the lower film cavity module, thus the change in height can be used to deduce the change in volume of the subject to be measured 610.

Moreover, the measurement apparatus for measuring a relationship between a degree of cure and a specific volume of a packaging material is further provided with a data processing module such as a processor for calculating the volume shrinkage of the subject to be measured based on the change in volume of the subject to be measured. The present disclosure then analyzes the volume shrinkage and the degree of cure of the subject to be measured in order to obtain a relationship between these two data. It should be noted that the data processing module can be provided inside or outside the measurement apparatus. In case of a data processing module outside the measurement apparatus, it can be realized, for example, as a data processing program installed in a computer for performing analysis calculations of measurements provided by the measurement apparatus.

The manners in which relationships between the volume shrinkage and the degree of cure is obtained are explained as follow.

First, a reaction kinetics model can be found by measuring temperature of the subject to be measured. A heat analysis technique called Differential Scanning calorimetry (DSC) can be used to measure the heat released during curing of a packaging material. As a curing reaction is proportional to the heat change of the curing reaction, graphs depicting the degree of cure according to change in temperature under three different heating rates of the packaging material can be obtained by experiments.

Figure 7A:
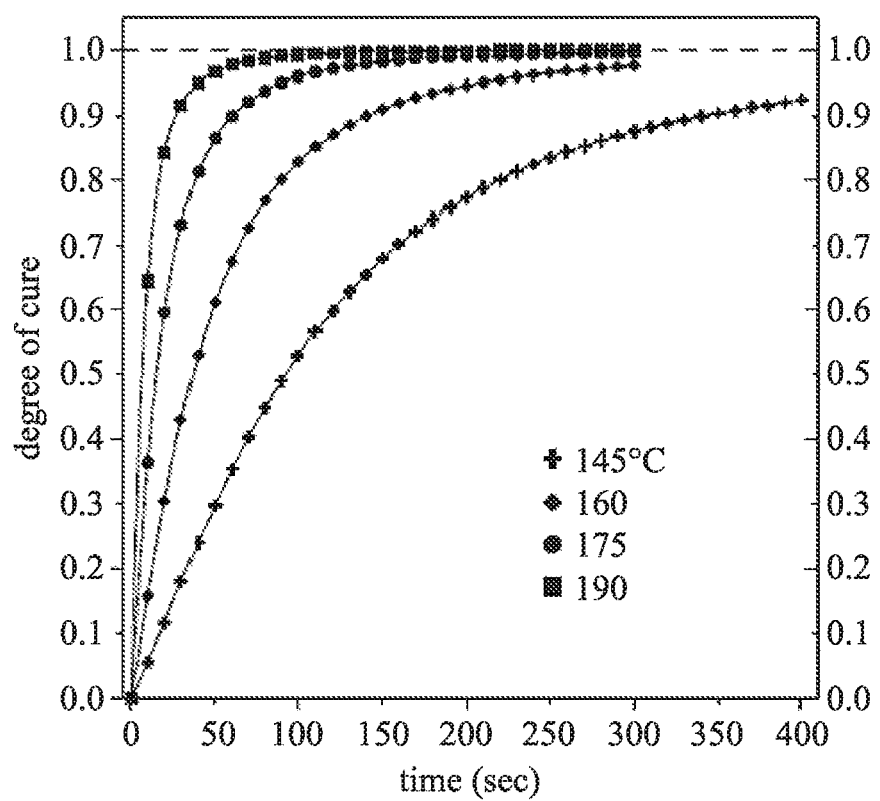
FIGS. 7A to 7C are graphs of experimental data showing a relationship between a volume shrinkage ratio and a degree of cure according to the present disclosure.

Upon obtaining graphs depicting the relationships between the degree of cure, the reaction rate and temperature during the curing reaction, data are inserted into a reaction kinetics model and a nonlinear regression analysis is performed to obtain parameters in the reaction kinetics model. Then, these parameters can be used to obtain a relationship graph of the degree of cure of the packaging material versus time under a constant temperature, such as that shown in FIG. 7A.

Figure 7B:
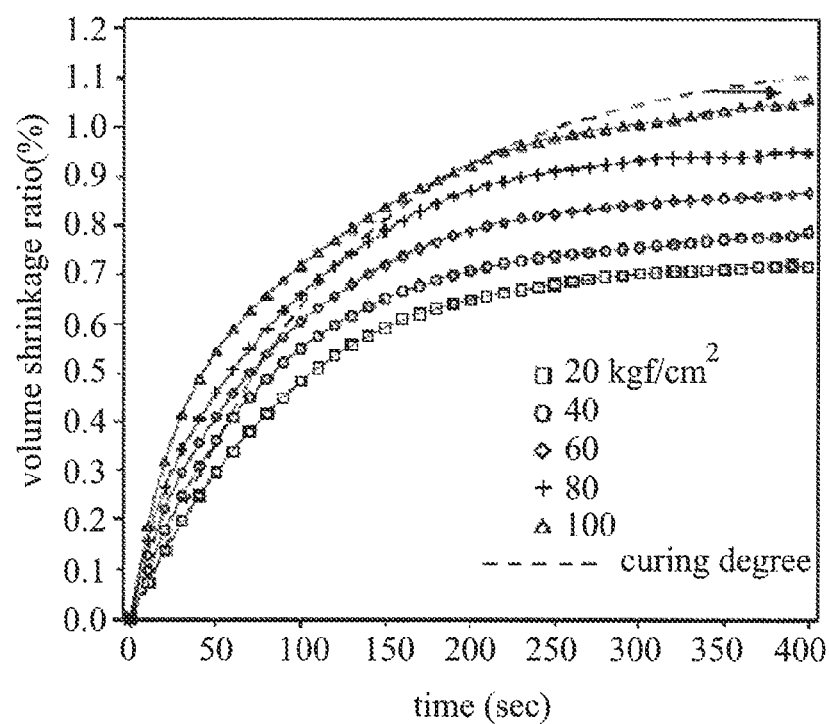

Next, experiments are performed under a plurality of constant pressures and constant temperature differences. When the packaging material is placed in the cavity, a period of time is needed for preheating to prevent material overflow. When the packaging material is squeezed in the cavity and volume shrinkage occurs, data is retrieved after pressure is equalized. Volume shrinkage ratio over time of the packaging material can be calculated according to the following formula (1).

$$VS_i(P_i t)_{T=const.} = \frac{V_o - V_i}{V_o} = \frac{h_o - h_i}{h_o} \quad (1)$$

wherein $VS_t$ is the Volume shrinkage ratio at an arbitrary time; $V_o$ is the initial volume; $V_i$ is the volume at an arbitrary time; $h_o$ is the initial height, and $h_i$ is the height at an arbitrary time. FIG. 7B is a graph showing the relationships of Volume shrinkage ratio and time under different pressures at 145° C. of a particular packaging material.

Finally, after the relationship graph of time versus degree of cure of the reaction kinetics model and the relationship graph of time versus Volume shrinkage ratio are combined, the relationship between volume shrinkage and degree of cure can be obtained, i.e., a "Pressure-Volume-Temperature-Curing (P-V-T-C)" relationship.

Figure 7C:
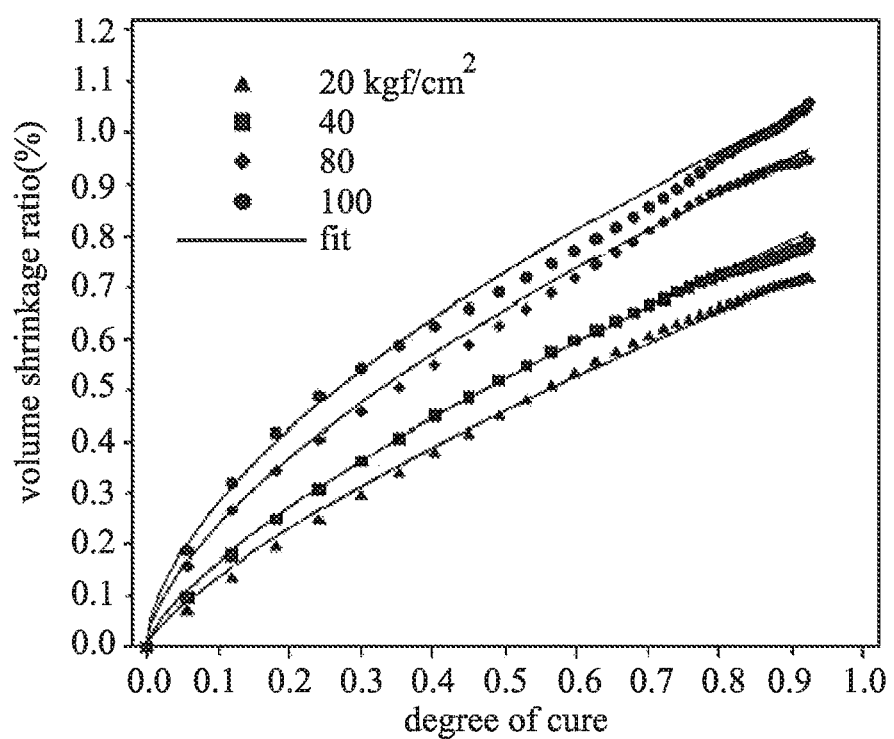

In an embodiment, the "P-V-T-C" relationship of a particular packaging material can be established, as shown in formula (2) below, wherein the various functions in formula (2) are shown in formulae (3) to (8). Through the "P-V-T-C" relationship, the relationship between volume shrinkage and degree of cure can be obtained. The Volume shrinkage ratios can be deduced for various different manufacturing processes.

$$VS(P,T,C) = F_1(P,T) \cdot C^{F_2(P,T)} \quad (2)$$

wherein $F_1(P,T)$ and $F_2(P,T)$ are functions of pressure (kgf/cm$^2$) and temperature (° C.), $$F_1(P,T) = f_a(T)P + f_b(T) \quad (3)$$

$$F_2(P,T) = f_c(T)P + f_d(T) \quad (4)$$

$$f_a(T) = a_2 T^2 + a_1 T + a_0 \quad (5)$$

$$f_b(T) = b_2 T^2 + b_1 T + b_0 \quad (6)$$

$$f_c(T) = c_2 T^2 + c_1 T + c_0 \quad (7)$$

$$f_d(T) = d_2 T^2 + d_1 T + d_0 \quad (8),$$

wherein $a_2$, $a_1$, $a_0$, $b_2$, $b_1$, $b_0$, $c_2$, $c_1$, $c_0$, $d_2$, $d_1$, and $d_0$ are material constants. FIG. 7C is a graph showing the relationships of volume shrinkage with temperature, pressure, and degree of cure at 145° C. of this particular packaging material. The above "P-V-T-C" relationship can be applied to warpage calculation of a packaging material.

In summary, a measurement apparatus for measuring a relationship between a degree of cure and a specific volume of a packaging material according to the present disclosure is capable of measuring the change in volume of a packaging material under different temperatures and pressure environments. After these data are obtained, the "P-V-T-C" relationship can be obtained, which can be used as a reference for calculating warpage of the packaging material during further packaging processes. This is more advantageous than merely considering the effect of temperature on warpage.

The above embodiments are only used to illustrate the principles of the present disclosure, and should not be construed as to limit the present disclosure in any way. The above embodiments can be modified by those with ordinary skill in the art without departing from the scope of the present disclosure as defined in the following appended claims.

What is claimed is:

1. An apparatus for measuring a relationship between a degree of cure and a specific volume of a packaging material, the apparatus comprising:

an upper load module provided at a top of the apparatus and including an upper servo motor, an upper ball screw and a force plate, with the upper servo motor configured for driving the upper ball screw into rotation via a belt, such that the force plate coupled to the upper ball screw moves downward to be positioned in place;

a lower load module provided at a bottom of the apparatus and including a lower servo motor, a lower ball screw and a load joint group having a push rod, with the lower ball screw configured for being driven by operations of the lower servo motor, such that the load joint group coupled to the lower ball screw creates a corresponding displacement;

an upper film cavity module coupled to the force plate of the upper load module; and a lower film cavity module provided on the lower load module for partially and slidably receiving the push rod of the load joint group, with the push rod configured for moving up with the displacement of the load joint group, wherein the lower film cavity module includes a cavity and a heating pipe configured for heating and maintaining a subject to be measured in the cavity at a constant temperature, wherein the upper load module is configured for moving down through the force plate and the push rod is configured for moving up in the lower film cavity module, such that a constant pressure is applied to the subject to be measured in the cavity, and a change in volume per unit time of the subject to be measured is measured by an optical measuring unit provided on the lower load module near the cavity.

2. The apparatus of claim 1, further comprising a controller connected to and configured for controlling operations of the upper servo motor, the lower servo motor, and the heating pipe based on a temperature, a load, and a displacement of the subject to be measured.

3. The apparatus of claim 2, wherein the controller is configured for adjusting the temperature of the heating pipe using a temperature controller.

4. The apparatus of claim 3, wherein the temperature controller is configured for obtaining the temperature of the subject to be measured using a temperature sensor provided in the cavity.

5. The apparatus of claim 2, wherein the controller is configured for obtaining forces exerted on the subject to be measured using a load sensor provided in each of the upper film cavity module and the lower film cavity module.

6. The apparatus of claim 5, wherein the controller is configured for converting the forces exerted on the subject to be measured into a voltage output, and the load of the subject to be measured is calculated based on a magnitude of the voltage.

7. The apparatus of claim 1, further comprising a data processing module connected to the controller and configured for calculating a volume shrinkage ratio of the subject to be measured based on the change in volume of the subject to be measured to obtain a relationship between the volume shrinkage ratio and the degree of cure of the subject to be measured.

8. The apparatus of claim 1, wherein the optical measuring unit is an optical ruler configured for measuring a change in a height of the subject to be measured.

9. The apparatus of claim 1, wherein the upper load module further includes a motor pulley coupled to the upper servo motor and a driven pulley coupled to the upper ball screw, with the belt surrounding the motor pulley and the driven pulley.

10. The apparatus of claim 1, further comprising an exterior frame configured for enclosing the upper load module, the lower load module, the upper film cavity module and the lower film cavity module.

11. The apparatus of claim 1, wherein the load joint group is provided at a top end of the lower ball screw, and the load joint group is configured for producing an upward displacement according to an upward movement of the lower ball screw.

12. The apparatus of claim 1, wherein the load joint group is provided at a side of the lower ball screw, and the load joint group is configured for producing an upward displacement along with an upward movement of the lower ball screw.

* * * * *